United States Patent
Anderson (10) Patent No.: US 7,158,754 B2
(45) Date of Patent: Jan. 2, 2007

(54) ELECTROMAGNETIC TRACKING SYSTEM AND METHOD USING A SINGLE-COIL TRANSMITTER

(75) Inventor: Peter Traneus Anderson, Andover, MA (US)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 393 days.

(21) Appl. No.: 10/611,112

(22) Filed: Jul. 1, 2003

(65) Prior Publication Data

US 2005/0003757 A1 Jan. 6, 2005

(51) Int. Cl.
*H04B 5/00* (2006.01)
*H04Q 7/20* (2006.01)
*A61B 5/05* (2006.01)
*G01C 9/00* (2006.01)
*G01R 33/02* (2006.01)

(52) U.S. Cl. .................. 455/41.1; 455/456.1; 600/424; 600/409; 702/152; 340/10.1; 340/539.13; 324/247

(58) Field of Classification Search ............... 456/41.1, 456/41.2, 456.1, 336, 337; 128/899; 600/424, 600/407, 409; 702/150–153; 340/10.1, 340/539.1–539.13; 324/207.22, 244, 247; 336/45

See application file for complete search history.

(56) References Cited

U.S. PATENT DOCUMENTS

| | | |
|---|---|---|
| 3,868,565 A | 2/1975 | Kuipers |
| 3,983,474 A | 9/1976 | Kuipers |
| 4,054,881 A | 10/1977 | Raab |
| 4,176,662 A | 12/1979 | Frazier |
| 4,613,866 A | 9/1986 | Blood |
| 4,618,822 A | 10/1986 | Hansen |
| 4,622,644 A | 11/1986 | Hansen |
| 4,642,786 A * | 2/1987 | Hansen ...................... 702/153 |
| 4,710,708 A * | 12/1987 | Rorden et al. ......... 324/207.26 |
| 4,737,794 A | 4/1988 | Jones |
| 4,742,356 A | 5/1988 | Kuipers |
| 5,099,845 A | 3/1992 | Besz et al. |
| 5,172,056 A * | 12/1992 | Voisin ................... 324/207.17 |
| 5,211,165 A | 5/1993 | Dumoulin et al. |

(Continued)

FOREIGN PATENT DOCUMENTS

WO WO 9949783 A 10/1999

OTHER PUBLICATIONS

Peter T. Anderson, A Source of Accurately Calculable Quasi-Static Magnetic Fields, Oct. 2001.

(Continued)

*Primary Examiner*—Duc M. Nguyen
(74) *Attorney, Agent, or Firm*—McAndrews, Held & Malloy, Ltd.; Peter J. Vogel; Micahel A. Dellapenna (57) ABSTRACT

Certain embodiments of the present invention provide a system and method for electromagnetic tracking using a single-coil transmitter. The system includes a single coil transmitter emitting a signal, a receiver receiving a signal from the single coil transmitter, and electronics for processing the signal received by the receiver. The electronics determine a position of the single coil transmitter. The transmitter may be a wireless or wired transmitter. The receiver may be a printed circuit board. In an embodiment, the receiver may be a twelve receiver circuit printed circuit board including single coils and/or pairs of coils. The electronics may determine position, orientation, and/or gain of the transmitter.

4 Claims, 4 Drawing Sheets

U.S. PATENT DOCUMENTS

| | | | |
|---|---|---|---|
| 5,245,307 A * | 9/1993 | Klaus et al. ................ 336/200 |
| 5,251,635 A | 10/1993 | Dumoulin et al. |
| 5,255,680 A | 10/1993 | Darrow |
| 5,265,610 A | 11/1993 | Darrow |
| 5,307,072 A * | 4/1994 | Jones, Jr. .................... 348/147 |
| 5,377,678 A | 1/1995 | Dumoulin et al. |
| 5,425,367 A | 6/1995 | Shapiro |
| 5,425,382 A | 6/1995 | Golden et al. |
| 5,429,132 A | 7/1995 | Guy et al. |
| 5,437,277 A | 8/1995 | Dumoulin |
| 5,443,066 A | 8/1995 | Dumoulin et al. |
| 5,445,150 A | 8/1995 | Dumoulin et al. |
| 5,517,195 A | 5/1996 | Narlow et al. |
| 5,558,091 A | 9/1996 | Acker |
| 5,592,939 A | 1/1997 | Martinelli |
| 5,622,169 A | 4/1997 | Golden et al. |
| 5,912,925 A * | 6/1999 | Palermo et al. ............. 375/258 |
| 6,009,878 A | 1/2000 | Haller et al. |
| 6,052,610 A | 4/2000 | Koch |
| 6,073,043 A * | 6/2000 | Schneider ................... 600/424 |
| 6,129,667 A | 10/2000 | Dumoulin |
| 6,129,668 A | 10/2000 | Haynor et al. |
| 6,177,792 B1 * | 1/2001 | Govari et al. .......... 324/207.12 |
| 6,188,355 B1 | 2/2001 | Gilboa |
| 6,201,987 B1 | 3/2001 | Dumoulin |
| 6,226,547 B1 | 5/2001 | Lockhart |
| 6,230,038 B1 | 5/2001 | von Gutfeld et al. |
| 6,233,476 B1 * | 5/2001 | Strommer et al. .......... 600/424 |
| 6,259,372 B1 | 7/2001 | Taranowski et al. |
| 6,369,564 B1 | 4/2002 | Khalfin et al. |
| 6,374,131 B1 * | 4/2002 | Tomita et al. ............... 600/409 |
| 6,374,134 B1 | 4/2002 | Bladen |
| 6,427,079 B1 | 7/2002 | Schneider et al. |
| 6,459,882 B1 | 10/2002 | Palermo et al. |
| 6,463,039 B1 | 10/2002 | Ricci |
| 6,472,975 B1 | 10/2002 | Beigel et al. |
| 6,474,341 B1 * | 11/2002 | Hunter et al. ................ 128/899 |
| 6,774,624 B1 * | 8/2004 | Anderson et al. ...... 324/207.17 |
| 6,822,570 B1 * | 11/2004 | Dimmer et al. .......... 340/572.1 |
| 2002/0030483 A1 * | 3/2002 | Gilboa .................. 324/207.17 |

OTHER PUBLICATIONS

Tom Ahlkvist Scharfeld, An Analysis of the Fundamental Constraints on Low Cost Passive Radio-Frequency Identification System Design, Aug. 2001.

* cited by examiner

ELECTROMAGNETIC TRACKING SYSTEM AND METHOD USING A SINGLE-COIL TRANSMITTER

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to an electromagnetic tracking system. In particular, the present invention relates to an electromagnetic tracking system using a single-coil wired or wireless transmitter.

Many medical procedures involve a medical instrument, such as a drill, a catheter, scalpel, scope, stent or other tool. In some cases, a medical imaging or video system may be used to provide positioning information for the instrument, as well as visualization of an interior of a patient. However, medical practitioners often do not have the use of medical imaging systems when performing medical procedures. Typically, medical imaging systems are too slow to produce useable real-time images for instrument tracking in medical procedures. The use of medical imaging systems for instrument tracking may be also limited for health and safety reasons (e.g., radiation dosage concerns), financial limitations, physical space restrictions, and other concerns, for example.

Medical practitioners, such as doctors, surgeons, and other medical professionals, often rely upon technology when performing a medical procedure, such as image-guided surgery or examination. A tracking system may provide positioning information of the medical instrument with respect to the patient or a reference coordinate system, for example. A medical practitioner may refer to the tracking system to ascertain the position of the medical instrument when the instrument is not within the practitioner's line of sight. A tracking system may also aid in presurgical planning.

The tracking or navigation system allows the medical practitioner to visualize the patient's anatomy and track the position and orientation of the instrument. The medical practitioner may use the tracking system to determine when the instrument is positioned in a desired location. The medical practitioner may locate and operate on a desired or injured area while avoiding other structures. Increased precision in locating medical instruments within a patient may provide for a less invasive medical procedure by facilitating improved control over smaller instruments having less impact on the patient. Improved control and precision with smaller, more refined instruments may also reduce risks associated with more invasive procedures such as open surgery.

Tracking systems may also be used to track the position of items other than medical instruments in a variety of applications. That is, a tracking system may be used in other settings where the position of an instrument in an object or an environment is unable to be accurately determined by visual inspection. For example, tracking technology may be used in forensic or security applications. Retail stores may use tracking technology to prevent theft of merchandise. In such cases, a passive transponder may be located on the merchandise. A transmitter may be strategically located within the retail facility. The transmitter emits an excitation signal at a frequency that is designed to produce a response from a transponder. When merchandise carrying a transponder is located within the transmission range of the transmitter, the transponder produces a response signal that is detected by a receiver. The receiver then determines the location of the transponder based upon characteristics of the response signal.

Tracking systems are also often used in virtual reality systems or simulators. Tracking systems may be used to monitor the position of a person in a simulated environment. A transponder or transponders may be located on a person or object. A transmitter emits an excitation signal and a transponder produces a response signal. The response signal is detected by a receiver. The signal emitted by the transponder may then be used to monitor the position of a person or object in a simulated environment.

Tracking systems may be ultrasound, inertial position, or electromagnetic tracking systems, for example. Electromagnetic tracking systems may employ coils as receivers and transmitters. Typically, an electromagnetic tracking system is configured in an industry-standard coil architecture (ISCA). ISCA uses three colocated orthogonal quasi-dipole transmitter coils and three colocated quasi-dipole receiver coils. Other systems may use three large, non-dipole, non-colocated transmitter coils with three colocated quasi-dipole receiver coils. Another tracking system architecture uses an array of six or more transmitter coils spread out in space and one or more quasi-dipole receiver coils. Alternatively, a single quasi-dipole transmitter coil may be used with an array of six or more receivers spread out in space.

Figure 4:
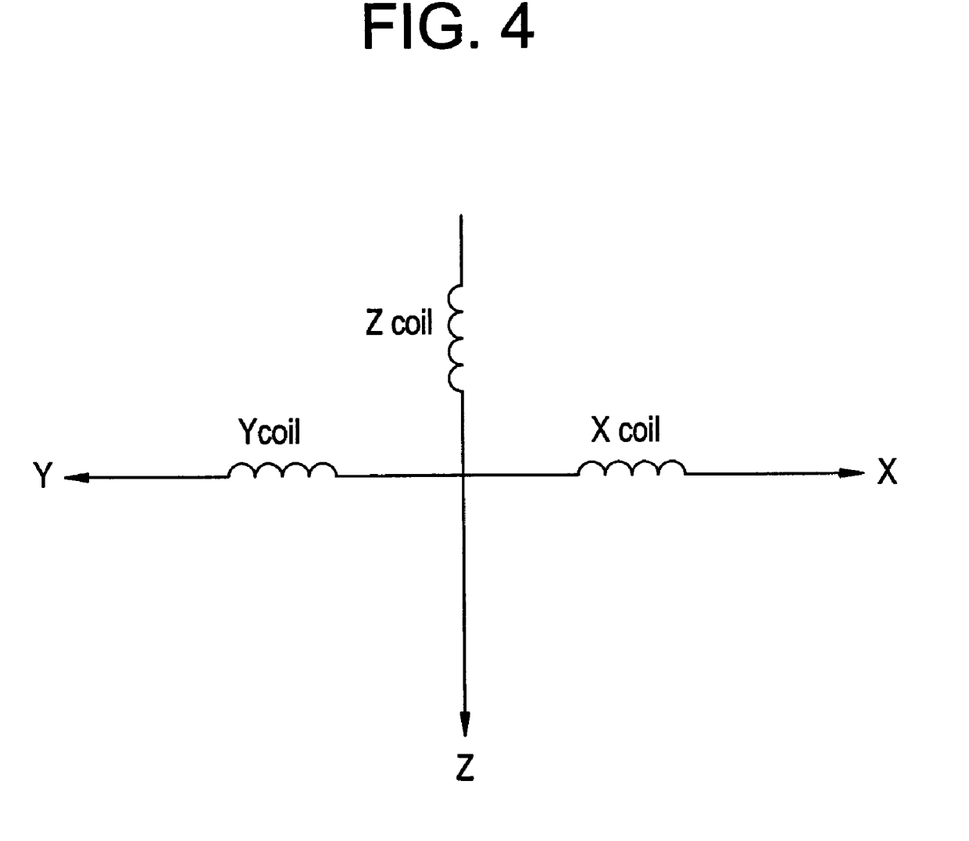
FIG. 4 illustrates a dipole coil trio used in accordance with an embodiment of the present invention.

The ISCA tracker architecture uses a three-axis dipole coil transmitter and a three-axis dipole coil receiver. Each three-axis transmitter or receiver is built so that the three coils exhibit the same effective area, are oriented orthogonally to one another, and are centered at the same point. An example of a dipole coil trio with coils in X, Y, and Z directions spaced approximately equally about a center point is shown in FIG. 4. If the coils are small enough compared to a distance between the transmitter and receiver, then the coil may exhibit dipole behavior. Magnetic fields generated by the trio of transmitter coils may be detected by the trio of receiver coils. Using three approximately concentrically positioned transmitter coils and three approximately concentrically positioned receiver coils, for example, nine parameter measurements may be obtained. From the nine parameter measurements and a known position or orientation parameter, a position and orientation calculation may determine position and orientation information for each of the transmitter coils with respect to the receiver coil trio with three degrees of freedom.

Some existing electromagnetic tracking systems include a transmitter and receiver wired to a common device or box. In system with the transmitter and receiver wired to a common device, the object being tracked is wired to the same device as the components performing the tracking. Thus, the range of motion of the object being tracked is limited.

Wireless electromagnetic tracking systems allow for the object being tracked to move freely without being limited by connections with the transmitter or receiver. To reduce the bulk associated with attaching a battery or other power source to a transponder, passive transponders may employ a coil as a means of coupling with and receiving power from other devices.

Typically, a transponder is located on or within a device in order to track movement of the device. In order to determine the transponder's location, a transmitter generates an excitation signal that is incident on the transponder. The incidence of the excitation signal on the transponder causes the transponder to emit a response signal. Typically, the response signal is emitted at the same frequency as the excitation signal.

The response signal emitted by the transponder and the excitation signal emitted by the transmitter are incident upon a receiving coil. Typically, in a tracking system using a passive transponder the excitation signal is much larger than the response signal when both signals are received at the receiver. Because the response signal is emitted at the same frequency as the excitation signal and the response signal is much smaller than the excitation signal, accurately separating and measuring the response signal is difficult.

Many instruments, such as catheters or flexible ear, nose and throat instruments, require a single small coil to be tracked. Current ISCA architectures track a trio of transmitter coils with a trio of receiver coils. Therefore, a need exists for an electromagnetic tracking system for tracking an instrument using a single coil.

Additionally, metal in many surgical instruments interferes with typical ISCA calculations for tracking. Thus, tracking is often inaccurate for metallic surgical instruments due to interference with magnetic fields. Thus, a system with improved, accurate tracking for use with metal instruments would be highly desirable.

Furthermore, receivers may need to be calibrated to help ensure accurate tracking of the transmitter. A calibration coil may be added to a receiver assembly. However, a calibration coil adds to thickness of the receiver assembly. Thus, each assembly is individually measured between the calibration and receiver coils. Thus, a calibration coil that does not add to the size or complexity of the tracking system would be highly desirable.

Thus, there is a need for an improved electromagnetic tracking system using a single-coil wired or wireless transmitter.

BRIEF SUMMARY OF THE INVENTION

Certain embodiments of the present invention provide a system and method for electromagnetic tracking using a single-coil transmitter. The system includes a single coil transmitter emitting a signal, a receiver receiving a signal from the single coil transmitter, and electronics for processing the signal received by the receiver. The electronics determine a position of the single coil transmitter.

The transmitter may be a wireless or wired transmitter. The single coil of the transmitter may be a dipole. The transmitter may be battery-powered. Additionally, the transmitter may be driven with a continuous wave signal.

The receiver may be a printed circuit board. Additionally, the receiver may be a twelve-receiver array. In an embodiment, the receiver may be a twelve receiver circuit printed circuit board. Four circuits may include single spiral coils. Eight circuits may include pairs of spiral coils.

The electronics may determine position, orientation, and/or gain of the transmitter. The electronics may determine a ratio of mutual inductance between the transmitter and the receiver to determine the position of the transmitter. The electronics may also determine a ratio of currents and/or magnetic fields produced at the transmitter to determine the position of the transmitter.

Certain embodiments provide an improved instrument tracking system including a single-coil wireless transmitter, a printed circuit board receiver array including a plurality of coils and coil pairs, and tracker electronics for analyzing parameter(s) between the transmitter and the coils and coil pairs of the receiver array to determine a position of the transmitter in relation to the receiver array. The parameters may include mutual inductances and/or magnetic fields. The tracker electronics may also determine a gain and/or an orientation of the transmitter. In an embodiment, reciprocity allows the coils of the receiver array to be treated as transmitter coils. The system may also include a calibration coil for calibrating the receiver array.

In an embodiment, the printed circuit board receiver array produces magnetic fields as follows: a mostly uniform field point in an X direction; a field varying mostly with X, pointed in the X direction; a field varying mostly with Y, pointed in the X direction; a field varying mostly with Z, pointed in the X direction; a mostly uniform field pointed in the Y direction; a field varying mostly with X, pointed in the Y direction; a field varying mostly with Y, pointed in the Y direction; a field varying mostly with Z pointed in the Y direction; a mostly uniform field pointed in the Z direction; a field varying mostly with X pointed in the Z direction; a field varying mostly with Y pointed in the Z direction; and a field varying mostly with Z pointed in the Z direction.

Certain embodiments provide a method for improved instrument tracking. The method includes driving a transmitter coil at a certain frequency to emit a signal and receiving the signal at an array of receiver coils. The method also includes determining a gain of the transmitter coil and measuring a mutual inductance between the transmitter coil and an array of receiver coils. An initial estimate of a position of the transmitter coil is selected. The initial estimate is adjusted using an error-minimizing routine based on the mutual inductance. The initial estimate may be a previous calculation result.

The method may also include calibrating the array of receiver coils. Additionally, the method may include eliminating a sign ambiguity of the gain of the transmitter coil. A transmitter current may also be determined from the signal received at the array of receiver coils.

In a certain embodiment, a method for electromagnetic tracking includes driving an array of coils at different frequencies, determining ratios of currents produced by the different frequencies, measuring voltages generated at the different frequencies, and calculating ratios of mutual inductances between the array of coils and a single coil located remotely from said array of coils. The method further includes estimating an initial value for at least one of position, gain, and orientation of the single coil and determining a best fit value for at least one of the position, gain, and orientation of the single coil based on the initial value and the ratios of mutual inductances. The method may also include calibrating the array of coils.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
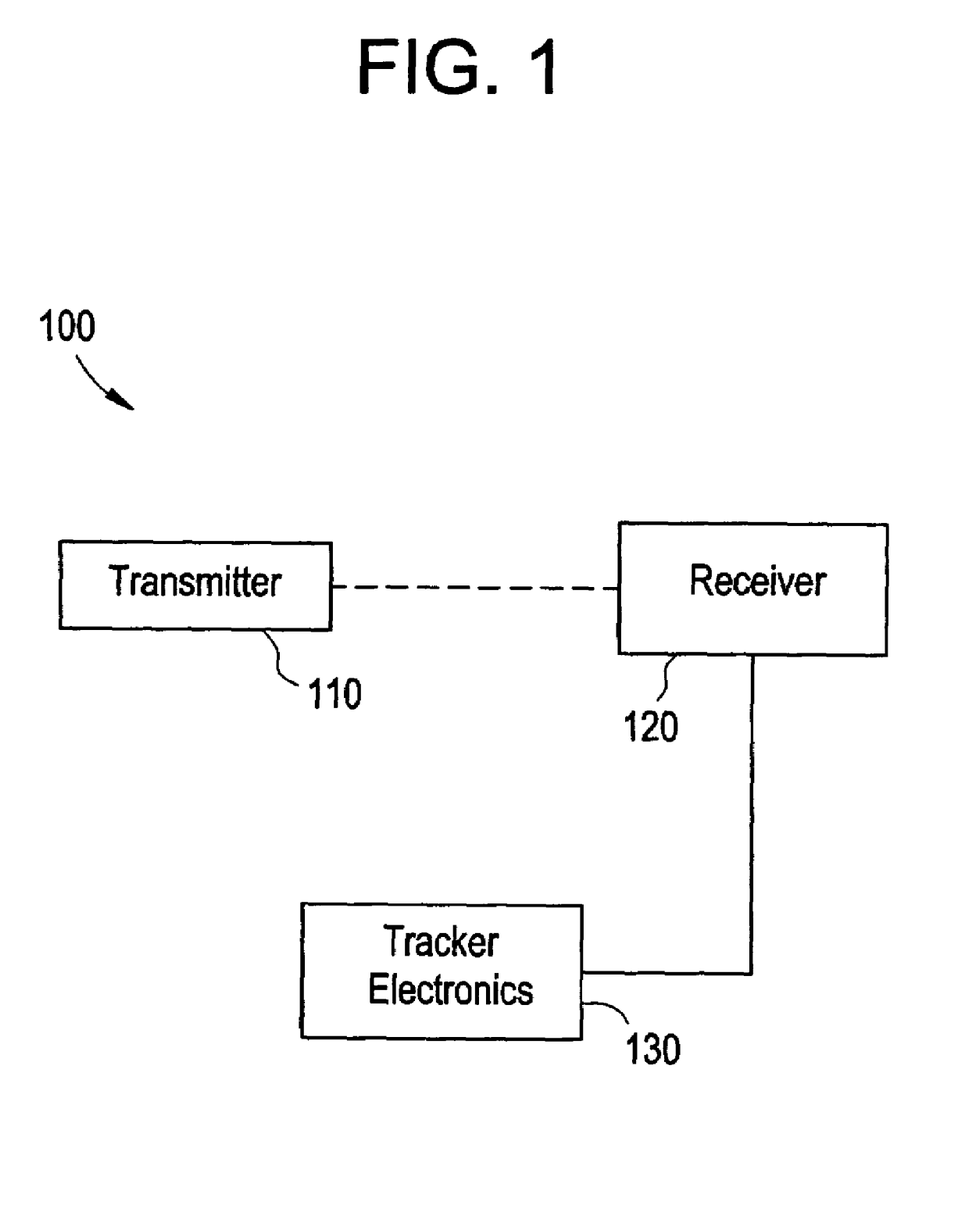
FIG. 1 illustrates a wireless tracker used in accordance with an embodiment of the present invention.

FIG. 1 illustrates a wireless tracker 100 used in accordance with an embodiment of the present invention. The wireless tracker 100 includes a wireless transmitter 110, a wired receiver 120, and tracker electronics 130. The wireless transmitter 110 transmits a signal. The wired receiver 120 detects the signal. The tracker electronics 130 analyze the received signal and relationship between the transmitter 110 and receiver 120 to determine a position of the transmitter 110.

In an embodiment, the wireless transmitter 110 is a single-coil wireless transmitter. The wireless transmitter 110 may be a battery-powered wireless transmitter. Alternatively, a single-coil wired transmitter may be used in place of or in addition to the wireless transmitter 110. In an embodiment, the wired receiver 120 is a twelve-coil wired receiver. Unlike a wireless receiver, the battery-powered wireless transmitter 110 does not need an auxiliary wireless channel for communicating with the receiver 120 and tracker electronics 130. A magnetic field emitted by the transmitter 110 allows both measurement of position and communication with the receiver 120 and the tracker electronics 130.

Some instruments, such as catheters and flexible ear, nose and throat (ENT) instruments, for example, may be tracked with a single small coil. In an embodiment, an instrument may be tracked with position information and without roll information.

In an embodiment, the coil of the wireless transmitter 110 is driven with a continuous wave (CW) sine wave (a 20 kHz sine wave, for example). A driver for the transmitter coil is powered by a 3 volt lithium cell, for example. The driver may be connected to the transmitter coil using a short cable (such as a 0.1 meter coaxial cable), for example. In an embodiment, the transmitter coil is 8 millimeters long and 1.7 millimeters in diameter. The transmitter coil is wound with 7700 turns of American Wire Gauge (AWG) 54 wire around a ferromagnetic core that is 8 millimeters long and 0.5 millimeters in diameter, for example.

The core increases an effective area of the coil by a factor of approximately:

$$\text{area\_factor} = \left(\frac{\text{coil\_length}}{\text{coil\_diameter}}\right)^2. \quad (1)$$

For example, the effective coil area factor is (8 mm/1.7 mm)²=22. The coil may be a coil manufactured by Maine Scientific or other manufacturer, for example.

The coil driver may not produce a precise current to drive the transmitter coil. Additionally, the effective area of the coil may not be precisely known or measured. As described below, an actual current in the coil may be calculated.

In an embodiment, the transmitter coil is small enough that the coil acts sufficiently like a dipole for tracking purposes. A dipole may be described by position, orientation, and gain (or strength). The position, orientation, and strength of the coil may be determined as described below. Therefore, the position, orientation, and gain of the wireless transmitter coil and the tracker electronics 130 may be determined without characterization.

Figure 2:
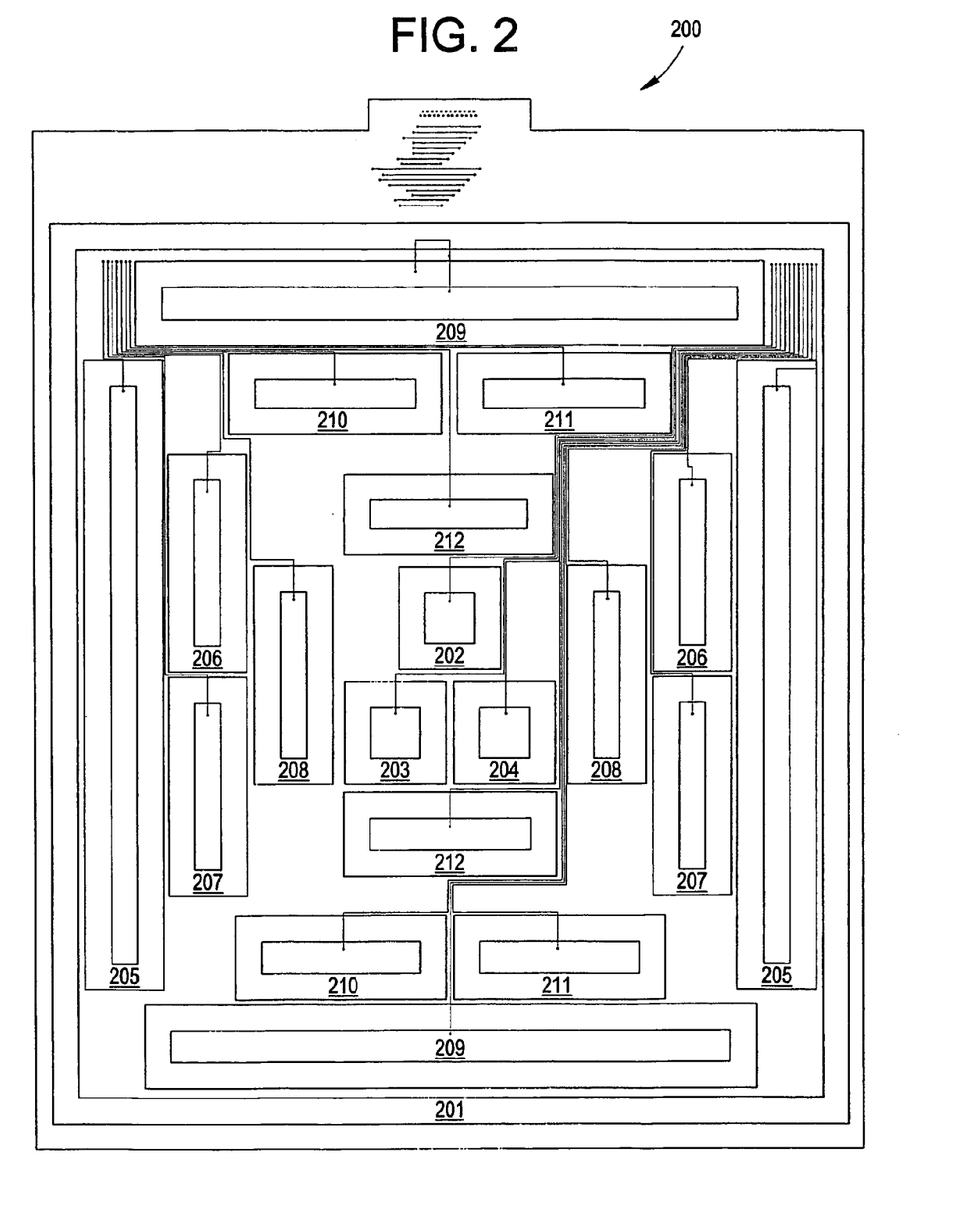
FIG. 2 shows a printed circuit board used in accordance with an embodiment of the present invention.

In an embodiment, the receiver 120 is a single 0.48 meter by 0.52 meter printed circuit board (PCB). The PCB may include 20 coils formed by copper tracks in the PCB, for example. The coils may be connected in series pairs and/or used individually, for example. In an embodiment, twelve separate conducting paths may be present on the PCB (called the ANT-009 design). PCB coils may be precisely made at a low cost. The ANT-009 PCB may be used as an array of transmitters or as an array of receivers, for example. FIG. 2 shows an embodiment of the ANT-009 PCB.

In an embodiment, receiver coils in the PCB are spread out or distributed on the PCB. The distributed coils are susceptible to electrostatic pickup. A Faraday shield may be used to block electrostatic pickup from the PCB without affecting electromagnetic signals received by the receiver 120.

Mutual inductance may be used in the electromagnetic tracking system to identify the positions of components in the system. Mutual inductance may allow the system to be divided into two parts: coils and electronics 130. Determining mutual inductance involves a physical design of the coils and a geometrical relationship between the coils but not details of the electronics 130 used to measure the mutual inductance. Additionally, mutual inductance does not depend on which coil receives an applied current.

In addition to the electronics 130 used to measure mutual inductance, a system including one transmitter coil and one receiver coil forms a four-terminal two-port network. A varying current injected into one coil induces a voltage in the other coil. The induced voltage V is proportional to the rate of change of the applied current I:

$$V = L_m(dI/dt) \quad (2),$$

wherein $L_m$ represents mutual inductance. $L_m$ is based on the geometry of the coils (closed circuits). $L_m$ is a ratio independent of applied current waveform or frequency. Thus, $L_m$ is a well-defined property that may be measured with reasonable precision.

The position, orientation, and gain (POG) of the transmitter 110 may be calculated with respect to a coordinate system of the receiver 120. POG determinations employ reciprocity to generate magnetic field models that treat PCB receiver coils as transmitter coils. Reciprocity indicates that a mutual inductance of a pair of coils is independent of which coil is driven. By using pairs of coils in series on the PCB, magnetic fields in XYZ directions and with XYZ gradients are formed in a "sweet spot" in relation to the PCB. For example, fields are formed 0.1–0.2 meters above the center of the PCB. In an embodiment, the PCB includes 12 distinct single coils and coil pairs. A variety of magnetic fields enhance numerical stability of the POG calculation.

In an embodiment, the gain of the single transmitter coil may be determined with 6 or more receiver coils. In an embodiment, a mutual inductance model provides 12 mutual inductances from the transmitter coil to each of the receiver coils as a function of POG. First, an initial estimate of POG may be selected. For example, a POG result from a previous measurement and calculation cycle may be used as an initial estimate or seed for a POG calculation. Then, an error-minimizing routine may be used to adjust the POG estimate. The POG estimate is adjusted to minimize a difference between measured and modeled mutual inductances.

If a sine wave transmitter drive is used and the receiver 120 calculation is phase-locked to the transmitter drive, a sign of the transmitter coil gain may not be determined. An unknown sign of the transmitter 110 gain may create ambiguity in the POG. For example, reversing the transmitter coil end-for-end has no effect on the POG. In an embodiment, tracking may start with the transmitter coil at an approximately determined POG. The POG may then be tracked from cycle to cycle. In an alternative embodiment, sign ambiguity of the transmitter gain may be eliminated. A phase or sign of the transmitter 110 sine wave may be determined directly with no memory (e.g., without previous calculations). The phase may be determined without a phase-locked loop.

A complex transmitter current (tx_current) may be expressed as a product of two factors:

$$tx\_current = tx\_current\_magnitude * tx\_current\_phase \quad (3),$$

where tx_current_magnitude is a magnitude of the transmitter 110 current, and tx_current_phase is a phase of the transmitter 110 current. In an embodiment, the magnitude of the transmitter 110 current is real, positive, and varies slowly. The magnitude of the transmitter current is proportional to the gain of the POG. Thus, transmitter current magnitude may be determined by a POG calculation. The transmitter current phase is a complex, unity magnitude value. The phase is recalculated from newest receiver 120 signal data for each cycle. Transmitter current phase may be different for each cycle's data.

In an embodiment, the largest magnitude received signal in a 12-receiver array is one of receivers 0, 5, and 11 of an array of 0 to 11. The three receiver coil boards 0, 5, and 11 have approximately orthogonal directional responses. That is, if the total signal is a reasonable size, at least one of the receiver boards 0, 5, and 11 receives a signal that is not small. For a receiver signal array, receiver signals 0, 5, and 11 may be tested to determine which receiver signal is largest in magnitude. The signal with the largest magnitude is designated receiver_signal[r].

A denormalized transmitter current phase may then be calculated as follows:

$$tx\_current\_phase\_denormalized = \text{sign} \frac{receiver\_signal[r]}{i2\pi}, \quad (4)$$

where the sign is either +1 or −1. Then the current phase may be normalized and the sign corrected:

$$tx\_current\_phase = \frac{tx\_current\_phase\_denormalized}{|tx\_current\_phase\_denormalized|}. \quad (5)$$

A transmitter 110 complex current may then be determined:

$$tx\_current = tx\_current\_mag * tx\_current\_phase \quad (6).$$

Without a second harmonic signal measurement, a sign may be chosen for each cycle to maintain a consistent sign of the receiver_signal[n] elements over time. In an embodiment, tracking of the transmitter 110 begins from a selected position, such as a calibration position, to make an initial sign choice (+ or −). A second harmonic current of the transmitter coil may be generated with an asymmetrical waveform including even harmonics and a CW fundamental frequency. For example, a transmitter coil driver may output an asymmetrical square wave voltage (for example, ⅓, ⅔ duty cycle) to drive the coil in series with a tuning capacitor. Alternatively, a diode (or a series combination of a diode and a resistor, for example) may be connected in parallel with the coil to generate even harmonics.

A harmonic frequency may be used to determine the sign of the fundamental frequency. The harmonic may be amplitude modulated with low-speed analog or digital data without affecting a tracking function. The data may be characterization data, data from a transducer mounted on the transmitter 110, or other data, for example.

In an embodiment, a low cost battery-powered transmitter driver and coil may be used. Cost may be reduced by not characterizing the single coil of the transmitter 110. The low cost driver and single coil may be used in disposable applications, for example.

If a transmitter unit 110 is sealed, such as in medical applications, activating or turning a unit "on and off" may present difficulties. In an embodiment, a transmitter driver includes a silicon CMOS chip with an on-off flip-flop or latch circuit and a photocell. A brief flash of light sets the flip-flop and activates the driver. Once set, the flip-flop remains set independent of illumination until a specific electromagnetic pulse resets the flip-flop and turns the driver off. After manufacture and testing, the driver-coil assembly may be packaged in a sealed, lightless container, such as a container used for photographic film. The packaged driver is turned off by applying an electromagnetic pulse. When a user opens the package, ambient light turns on the driver. The driver runs until receiving an electromagnetic pulse or until energy in a driver battery is exhausted.

The transmitter 110 may be driven by an oscillator powered by direct current, for example. In an embodiment, the wired transmitter driver may be powered from a source of 3 volts at a milliampere direct current. For example, photocells powered by ambient light may power the driver. Alternatively, radio frequency energy may be rectified to power the driver.

In one embodiment, a single transmitter coil is located at the tip of a catheter. A small silicon photocell is connected across the coil. The photocell is illuminated with amplitude-modulated light. The photocell powers a driver for the transmitter coil. Alternatively, two photocells may be connected in antiparallel across the transmitter coil. By alternately illuminating each photocell, an alternating current may be generated in the coil.

Alternate illuminations may be achieved using two optical fibers (one to each photocell). Illumination may also be achieved using one fiber to illuminate the photocells through filters of different polarizations or different colors, for example. In another embodiment, two photocells may be integrated on top of each other. Each photocell may be sensitive to different wavelengths of light.

An optically powered coil may have advantages over an electrically powered coil. For example, optical fibers may be smaller than electrical wires. Additionally, a catheter, for example, with an optically powered coil has no electrical energy in most of the length of the catheter. An electrically powered coil may result in some electrical energy in the catheter.

In another embodiment, the receiver 120 may include an array(s) of three-axis dipole wire-wound coil trios. Due to inaccuracies in coil winding, the receiver 120 is characterized before use in tracking. The wire-wound receiver coil arrangement may have a better signal-to-noise ratio than a PCB coil, due to a larger volume of copper in a wound coil of a given volume. Additionally, POG seed algorithms may be used with characterized receiver coils.

In an alternative embodiment, a battery-powered wireless transmitter driver receives a clock signal from the tracker electronics 130 via a magnetic, radio frequency, ultrasonic, or other signal generator. A clock signal may eliminate phase-locking and ambiguity in the sign of the transmitter gain.

In another embodiment, the wireless transmitter 110 may be combined with various wireless radio frequency identification (RFID) schemes. RFID techniques allow for identification and/or data transfer without contact between the transmitter 110 and the receiver 120. The wireless transmitter 110 may be used with RFID technology to transmit data to the receiver 120 and tracker electronics 130.

As described above, a PCB may be used in an electromagnetic tracking system, such as the wireless tracker 100. The following discussion illustrates an embodiment of the PCB in more detail. The PCB may be configured as a transmitter coil array and be used to track a single receiver coil against an array of twelve transmitter coils, for example. The PCB may also be configured as a receiver coil array and used to track a single-coil transmitter. The PCB may be used as the receiver 120 in the wireless tracker 100 tracking the single-coil transmitter 110. Reciprocity allows coils in the receiver coil array to be treated as transmitter coils.

In an embodiment, the PCB is precisely manufactured, so a magnetic field model of the PCB may be determined with sufficient accuracy without characterization. A single coil transmitter is small enough to be modeled with sufficient accuracy as a dipole with a position, orientation, and gain that are determined through tracking without characterization. In an embodiment, the PCB does not include curved traces. Magnetic fields may be more precisely calculated with straight line segments.

The POB board, such as the ANT-009 coil board 200 described above and shown in FIG. 2, may facilitate tracking around a small volume "sweet spot" located over the center of the PCW In an embodiment, the board provides magnetic fields in the sweet spot that are approximately as follows:

1. a mostly uniform field pointed in the X direction;
2. a field varying mostly with X pointed in the X direction;
3. a field varying mostly with Y pointed in the X direction;
4. a field varying mostly with Z pointed in the X direction;
5. a mostly uniform field pointed in the Y direction;
6. a field varying mostly with X pointed in the Y direction;
7. a field varying mostly with Y pointed in the Y direction;
8. a field varying mostly with Z pointed in the Y direction;
9. a mostly uniform field pointed in the Z direction;
10. a field varying mostly with X pointed in the Z direction;
11. a field varying mostly with Y pointed in the Z direction; and
12. a field varying mostly with Z pointed in the Z direction.

The X and Y directions are in the plane of the PCB. The Z direction is perpendicular to the plane of the PCB.

In an embodiment, the ANT-009 coil PCB 200 includes twelve separate electrical circuits. Four of the circuits include single spiral coils 201–204. Eight of the circuits include pairs of spiral coils 205–212. The single coils 201–204 generate non-uniform fields. The non-uniform fields generated by the single coils 201–204 are generated mostly in the Z direction at the sweet spot. Two coils in a pair 205–212 of spiral coils are positioned side-by-side. The coils are connected in series. Opposing coils connected in series produce non-uniform fields pointed mostly in the X and Y directions at the sweet spot. A single large coil 201 generates a mostly uniform Z field. A pair 205 of long narrow spirals on opposite edges of the PCB generates a mostly uniform X field. Another pair 209 of long narrow spirals on the other pair of opposite edges of the PCB generates a mostly uniform Y field.

The PCB 200 utilizes an approximate nature of the "mostly uniform" fields to produce an effect of the desired "varying mostly" fields. The "mostly uniform" fields may have gradients. For example, consider the Z-direction fields. One large coil 201 generates a "mostly uniform" Z field. Three small coils 202–204 may be placed near the origin of the PCB and offset from the origin along lines at roughly 0 degrees, 120 degrees, and 240 degrees. The three small coils 202–204 generate smaller "mostly uniform" Z fields displaced from the main "mostly uniform" Z field generated by the large coil. The effects of the "mostly varying" fields may be produced by taking sums and differences among the four fields discussed above. Fields in the X and Y directions may be generated similarly. However, connected pairs of series-opposing coils 206–208 (X-direction), 210–212 (Y-direction) may be used instead of single coils to generate fields in the X and Y directions. The above fields maybe calculated using a straight line segment field model, for example.

In an embodiment, the tracker electronics 130 includes twelve receiver coil drivers. The twelve coil drivers operate at twelve different CW frequencies, for example. The twelve coil drivers drive twelve receiver coil circuits on the receiver PCB. Currents in the twelve receiver coil circuits are measured. In an embodiment, current values are approximately determined. Then, ratios of the currents are determined.

Current in the coils causes the receiver coil circuits to emit magnetic fields. The magnetic fields induce voltages in a single transmitter coil at the twelve driver frequencies. The tracker electronics 130 measures signals at the twelve frequencies.

A mutual inductance between each receiver circuit and the transmitter coil is calculated. Mutual inductances between the transmitter 110 and receiver 120 are determined. In an embodiment, mutual inductances are approximately determined. Then, ratios of the twelve mutual inductances are determined. Six or more receiver coils spread in a selected configuration and measurements of the ratios of the mutual inductances to the transmitter coil may be used to calculate a position of the transmitter coil, an orientation (except roll) of the transmitter coil, and a gain of the transmitter coil (a POG determination). The gain of the transmitter coil represents a scale factor that converts the mutual inductance ratios into mutual inductance values (in Henries, for example).

In an alternative embodiment, a single-receiver-coil version PCB may be used to characterize three coils in an ISCA receiver or transmitter coil trio. The characterization process includes separately tracking each of the three ISCA coils for position, orientation, and gain. Then, the tracking data are combined into a coil characterization format used by ISCA trackers, for example.

Figure 3:
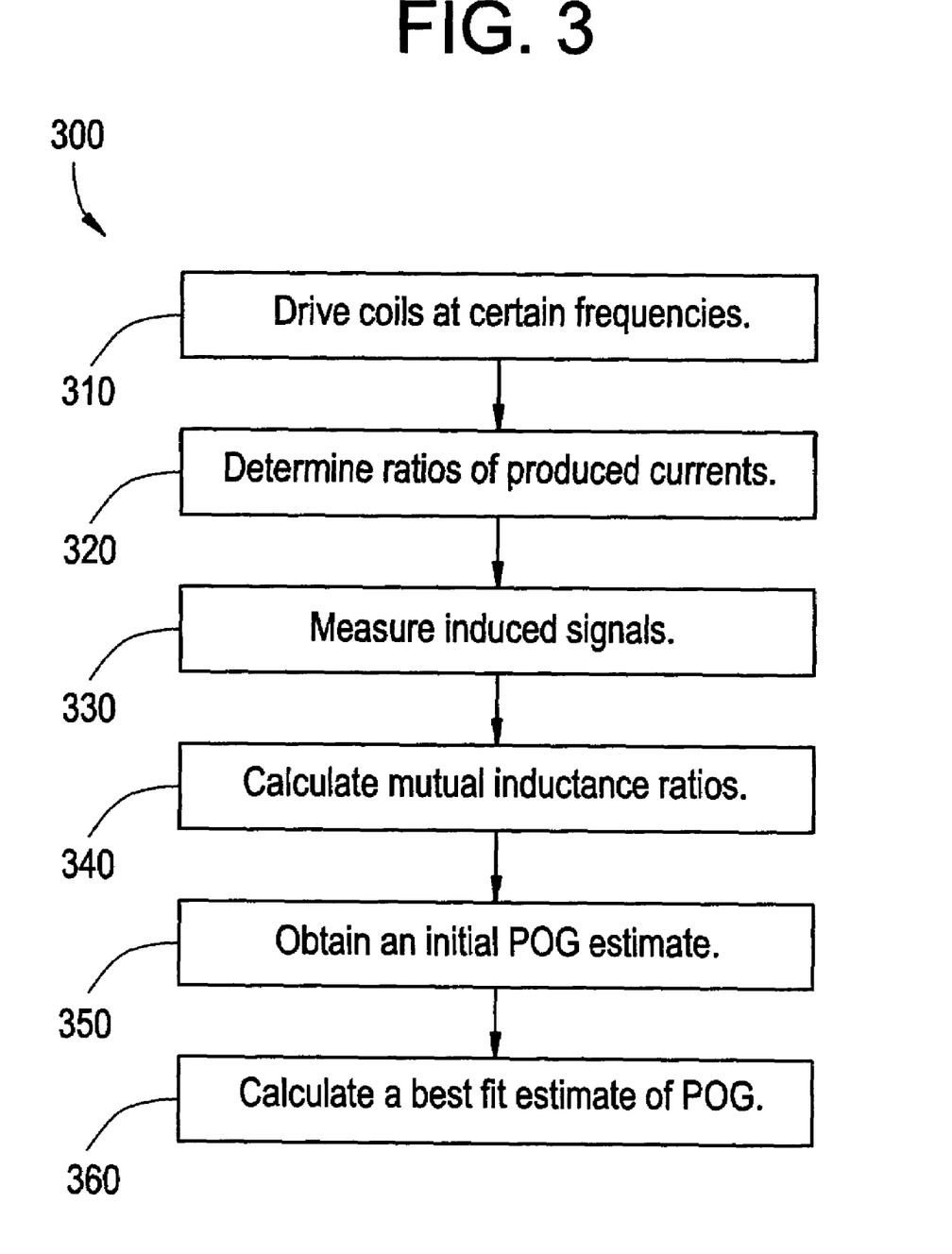
FIG. 3 depicts a flow diagram for a method for a position, orientation and gain determination used in accordance with an embodiment of the present invention.

FIG. 3 depicts a flow diagram for a method 300 for a POG determination used in accordance with an embodiment of the present invention. First, at step 310, receiver coils are driven at different frequencies. Drivers produce currents in the receiver coils. Then, at step 320, ratios of the currents produced in the receiver coils are determined. The receiver coils generate magnetic fields that induce voltages at different frequencies in the transmitter coil. At step 330, the signals induced at the transmitter coil are measured.

The voltages and currents produce mutual inductances between the transmitter coil and the receiver coils. At step 340, ratios of the mutual inductances between the receivers and the transmitter are calculated.

Next, at step 350, an initial estimate, or seed, of transmitter position, orientation, and gain is obtained. The estimate may be generated from prior mechanical knowledge of the transmitter POG, from a final POG estimate from a previous tracking cycle, or from a direct calculation from the mutual inductance measurements, for example.

Then, at step 360, a best-fit estimate of the POG to the mutual inductance ratio measurements may be calculated. The best-fit estimate may be calculated using a model of the transmitter-to-receiver mutual inductances and the seed POG values, for example. The best fit calculation may be any of several well-known solution fitting algorithms, such as least squares, Powell, and Levenberg-Marquardt, for example.

The above calculations may also be performed with the PCB configured as a twelve transmitter coil board with a single receiver coil. Additionally, the PCB may be configured with different numbers of coils to function as a transmitter and/or receiver.

In an embodiment, electromagnetic tracking systems calibrate receiver electronics to help ensure accurate positional measurements, for example. A calibration coil may be placed diagonally in a receiver coil assembly to provide approximately equal mutual inductances from the calibration coil to each of the receiver coils. The mutual inductances may be individually measured during manufacture. The mutual inductance values measured during manufacture may be stored in a characterization memory, for example. The measured mutual inductances may be used during tracking to calibrate the receiver electronics.

The PCB may include a calibration coil. The calibration coil may improve the usefulness of the PCB as a receiver 120. In an embodiment, the calibration coil is built on an inner layer or layers of the printed circuit assembly. The calibration coil may partially overlap existing coils in the assembly to produce desired calibration coil to receiver coil mutual inductances. In an embodiment, a single-turn calibration coil in a rectangle covering approximately one corner quadrant of the PCB is used.

In an embodiment, the calibration coil is part of a single PCB, rather than a separately fabricated addition. Thus, the calibration coil is in approximately the same plane as the receiver coils. Mutual inductances between the calibration coil and the receiver coils may be fixed by a fabrication process and calculated without measuring separate boards, for example. Alternatively, a separate calibration module may be added to measure small mutual inductances or mutual impedances separate from the coil assembly.

Ratios of transmitter 110 currents to a reference current in the calibration coil may be determined, for example. The calibration coil may have a defined mutual inductance with respect to each receiver coil. The mutual inductances, combined with measured current ratios, allow determination of transmitter-to-receiver mutual inductances from the measured ratios. If a wireless transmitter is used, current ratios may not be measured. Another measurement, such as magnetic field ratios, may be used with wireless transmitters.

Thus, certain embodiments of the PCB provide transmitter and receiver coils that do not need precise characterization. Certain embodiments use pairs of coils in series to generate magnetic fields parallel to the plane of the PCB while reducing the number of separate coil drivers used. For the ANT-009coil board, 12 drivers are used. A separate-coil version of the ANT-009 may use 20 drivers. Additionally, the straight line segments of the PCB allow use of an analytical model of a magnetic field due to a straight line current segment. Furthermore, expressions for mutual inductance between two straight line current segments may be used. Certain embodiments of the PCB also provide for calibration of the receiver and tracker electronics.

Certain embodiments of the present invention provide an electromagnetic tracking system including a wired or wireless transmitter with a single-coil. In an embodiment, one receiver coil assembly, whether PCB or wire-wound, may be used to simultaneously track a plurality of wireless and/or wired transmitters on different frequencies.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. An electromagnetic tracking system, said system comprising:
   a single coil transmitter generating a signal;
   a receiver receiving said signal from said single coil transmitter, wherein said receiver comprises a twelve receiver circuit printed circuit board; and
   electronics for processing said signal received by said receiver, said electronics determining a position of said single coil transmitter based at least in part on said signal,
   wherein four circuits include single spiral coils and eight circuits include pairs of spiral coils.

2. An improved instrument tracking system, said system comprising:
   a single-coil wireless transmitter, wherein said transmitter is adapted to generate an electromagnetic field;
   a printed circuit board receiver array including a plurality of coils and coil pairs, wherein said receiver array is adapted to receive said electromagnetic field from said single-coil wireless transmitter; and
   tracker electronics for analyzing at least one parameter between said transmitter and said coils and coil pairs of said receiver array to determine a position of said transmitter in relation to said receiver array based at least in part on said electromagnetic field
   wherein said printed circuit board receiver array produces magnetic fields comprising:
      a mostly uniform field point in an X direction;
      a field varying mostly with X, pointed in the X direction;
      a field varying mostly with Y, pointed in the X direction;

a field varying mostly with Z, pointed in the X direction;
a mostly uniform field pointed in the Y direction;
a field varying mostly with X, pointed in the Y direction;
a field varying mostly with Y, pointed in the Y direction;
a field varying mostly with Z pointed in the Y direction;
a mostly uniform field pointed in the Z direction;
a field varying mostly with X pointed in the Z direction;
a field varying mostly with Y pointed in the Z direction; and
a field varying mostly with Z pointed in the Z direction.

3. An electromagnetic tracking system, said system comprising:
a single coil transmitter emitting a signal;
a receiver receiving a signal from said single coil transmitter, wherein said receiver comprises a twelve receiver circuit printed circuit board, and wherein four circuits include single spiral coils and eight circuits include pairs of spiral coils; and
electronics for processing said signal received by said receiver, said electronics determining a position of said single coil transmitter.

4. An improved instrument tracking system, said system comprising:
a single-coil wireless transmitter;
a printed circuit board receiver array including a plurality of coils and coil pairs, wherein said printed circuit board receiver array produces magnetic fields comprising:
a mostly uniform field point in an X direction;
a field varying mostly with X, pointed in the X direction;
a field varying mostly with Y, pointed in the X direction;
a field varying mostly with Z, pointed in the X direction;
a mostly uniform field pointed in the Y direction;
a field varying mostly with X, pointed in the Y direction;
a field varying mostly with Y, pointed in the Y direction;
a field varying mostly with Z pointed in the Y direction;
a mostly uniform field pointed in the Z direction;
a field varying mostly with X pointed in the Z direction;
a field varying mostly with Y pointed in the Z direction; and
a field varying mostly with Z pointed in the Z direction; and
tracker electronics for analyzing at least one parameter between said transmitter and said coils and coil pairs of said receiver array to determine a position of said transmitter in relation to said receiver array.

* * * * *